(12) United States Patent
Shukov (10) Patent No.: US 6,344,055 B1
(45) Date of Patent: Feb. 5, 2002

(54) METHOD FOR PRODUCTION OF AN EXPANDABLE STENT

(75) Inventor: George A. Shukov, Los Altos Hills, CA (US)

(73) Assignee: Novo RPS ULC, Vancouver (CA)

( * ) Notice: Subject to any disclaimer, the term of this patent is extended or adjusted under 35 U.S.C. 154(b) by 0 days.

(21) Appl. No.: 09/423,813
(22) PCT Filed: May 14, 1998
(86) PCT No.: PCT/CA98/00471
 § 371 Date: Sep. 27, 2000
 § 102(e) Date: Sep. 27, 2000
(87) PCT Pub. No.: WO98/51238
 PCT Pub. Date: Nov. 9, 1998

Related U.S. Application Data
(60) Provisional application No. 60/046,497, filed on May 14, 1997.

(51) Int. Cl.[7] .................................................. A61F 2/06
(52) U.S. Cl. ...................... 623/1.15; 623/1.17; 623/901; 29/896.6
(58) Field of Search ................................ 623/1.15, 901, 623/1.17; 606/1; 29/896.6

(56) References Cited

U.S. PATENT DOCUMENTS

| 5,496,365 | A |   | 3/1996 | Sgro |
| 5,725,519 | A | * | 3/1998 | Penner et al. ................... 606/1 |
| 5,893,867 | A | * | 4/1999 | Bagaoisan et al. ........... 606/198 |
| 5,922,020 | A | * | 7/1999 | Klein et al. ..................... 623/1 |

FOREIGN PATENT DOCUMENTS

| EP |  0714641  | 6/1996 |
| WO | WO9704721 | 2/1997 |

* cited by examiner

Primary Examiner—Michael H. Thaler
(74) Attorney, Agent, or Firm—Katten, Muchin & Zavis (57) ABSTRACT

A method for producing an expandable stent includes steps of: (i) selectively removing portions of a solid tubular wall having a diameter substantially the same as that of the stent in a second, expanded position to define multiple sections of the porous surface connected to one another by a series of axially disposed connecting members; (ii) radially compressing the stent by applying a radially inward force on the multiple sections and the connecting members such that the multiple sections have a diameter substantially the same as that of the stent in the first, compressed position; and (iii) removing the connecting members between the multiple sections to produce the stent in the first position.

14 Claims, 7 Drawing Sheets

METHOD FOR PRODUCTION OF AN EXPANDABLE STENT

This application is a 371 of PCT/CA98/00471 May 14, 1998 which claims benefit to Ser. No. 60/046497 filed May 14, 1997.

TECHNICAL FIELD

The present invention relates to an expandable stent and to a method for production of same.

BACKGROUND ART

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g. a lumen or artery).

In the past six to eight years, the use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g. natural or iatrogenic) within the human body and can include a member selected from the group comprising: blood vessels, respiratory ducts, gastrointestinal ducts and the like.

Stent development has evolved to the point where the vast majority of currently available stents rely on controlled plastic deformation of the entire structure of the stent at the target body passageway so that only sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby plastically deforming the entire structure of the stent so that the latter is urged in place against the body passageway. As indicated above, the amount of force applied is at least that necessary to expand the stent (i.e., the applied the force exceeds the minimum force above which the stent material will undergo plastic deformation) while maintaining the patency of the body passageway. At this point, the balloon is deflated and withdrawn within the catheter, and is subsequently removed. Ideally, the stent will remain in place and maintain the target area of the body passageway substantially free of blockage (or narrowing).

See, for example, any of the following patents:

U.S. Pat. No. 4,733,665 (Palmaz),
U.S. Pat. No. 4,739,762 (Palmaz),
U.S. Pat. No. 4,800,882 (Gianturco),
U.S. Pat. No. 4,907,336 (Gianturco),
U.S. Pat. No. 5,035,706 (Gianturco et al.),
U.S. Pat. No. 5,037,392 (Hillstead),
U.S. Pat. No. 5,041,126 (Gianturco),
U.S. Pat. No. 5,102,417 (Palmaz),
U.S. Pat. No. 5,147,385 (Beck et al.),
U.S. Pat. No. 5,282,824 (Gianturco),
U.S. Pat. No. 5,316,023 (Palmaz et al.),
Canadian patent 1,239,755 (Wallsten), and
Canadian patent 1,245,527 (Gianturco et al.), the contents of each of which are hereby incorporated by reference, for a discussion on previous stent designs and deployment systems.

While prior stents which are reliant on plastic deformation of the entire stent structure for deployment have achieved a certain degree of success, they do suffer from some disadvantages. One particular disadvantage is that the stent structure is susceptible to the occurrence of "micro-cracks"—i.e., cracks of relatively small width and depth—especially in curved regions of the stent structure. Also, plastic deformation can lead to the occurrence of uneven thinning of the stent material. The occurrence of such cracks and/or uneven thinning can lead to weakened radial rigidity of the stent which, in turn, can lead to devastating consequences for the patient. Additionally, the many of the prior art stents are time consuming and expensive to produce.

Published International patent application WO 95/26695 [Lau et al. (Lau)] teaches a self-expandable, foldable stent which may be delivered using a catheter or other technique. The purported point of novelty in Lau relates to a stent which may be folded along its longitudinal axis. The folding is accomplished by conferring bending and twisting stresses to the stent, which stresses, for the material used to produce the stent, do not exceed that minimum stresses above which plastic deformation of the stent will occur—i.e., application of these stresses to the stent results in the storage of mechanical energy in the stent but does not result in the occurrence of any plastic deformation. The stent disclosed by Lau is disadvantageous since a relatively complicated folding protocol is needed. Specifically, in the illustrated embodiments, Lau teaches that the stent is folded into "a loose-C configuration" (FIGS. 33A and 33B), "a rolled configuration" (FIGS. 33C and 33D) or "a triple lobed configuration" (FIGS. 33E and 33F). The stent taught by Lau is also disadvantageous since, after it is folded (and thus contains the bending/twisting stresses described above), the stent must be restrained mechanically from spontaneous expansion—see, for example, FIGS. 35A, 35B, 36A, 36B, 39 and 40 of Lau which illustrate complicated tethering systems for mechanically restraining the folded stent from spontaneous expansion.

Published European patent application 0,669,114A [Fischell et al. (Fischell)] teaches a stent having a multiplicity of closed circular structures connected by a series of longitudinals. The stent is initially produced in a pre-deployment form comprising ovals connected by the longitudinals (see FIGS. 4 and 5). The pre-deployment form of the stent is than placed on the end of a balloon stent delivery catheter and the ovals are folded about their minor axis by securing the ovals at each end of the structure and translating a pair of opposed longitudinals (see FIG. 6). A disadvantage of this approach is that, during the folding step, plastic deformation of the stent structure unavoidable since folding is accomplished by securing selected portions of the stent while translating other portions of the stent. As discussed above, while this is disadvantageous during expansion of the stent, the disadvantages are heightened if the stent undergoes plastic deformation during adaption of the unexpanded stent to a delivery system prior to expansion. A further disadvantage of this approach is the need have distinct unfolded pre-deployment (i.e., post-production/no balloon), folded pre-deployment (i.e., on balloon) and post-deployment forms of the stent.

Accordingly, it would be desirable to have an improved stent which overcomes these disadvantages. It would be further desirable if the improved stent could be manufactured readily.

DISCLOSURE OF INVENTION

It is an object of the present invention to provide a novel expandable stent which obviates or mitigates at least one of the above-mentioned disadvantages of the prior art.

It is another object of the present invention to provide a novel method for manufacturing an expandable stent.

Accordingly, in one of its aspects, the present invention provides an expandable stent comprising a proximal end and a distal end in communication with one another, a tubular wall disposed between the proximal end and the distal end, the tubular wall having a longitudinal axis and a porous surface defined by a plurality of interconnecting struts, a series of the struts connected to one another at an interconnection point, the struts being reversibly hingable at the interconnection point between a first, contracted position and a second, expanded position, the stent being unrestrained in and expandable from the first position to the second position upon the application of a radially outward force on the stent.

In another of its aspects, the present invention provides an expandable stent comprising a proximal end and a distal end in communication with one another, a tubular wall disposed between the proximal end and the distal end, the tubular wall having a longitudinal axis and a porous surface defined by a plurality of interconnecting struts, a series of the struts connected to one another at a plastically bendable interconnection point, the struts being reversibly hingable at the plastically bendable interconnection point between a first, contracted position and a second position, expanded position, the stent being expandable from the first position to the second position upon the application of a radially outward force on the stent.

In yet another of its aspects, the present invention provides a process for producing a stent comprising a proximal end and a distal end in communication with one another, a tubular wall disposed between the proximal end and the distal end, the tubular wall having a longitudinal axis and a porous surface defined by a plurality of interconnecting struts, a series of the struts connected to one another at an interconnection point, the struts being reversibly hingable at the interconnection point between a first, unrestrained contracted position and a second, expanded position, the process comprising the step of applying a radially compressing the stent in the second position to produce the stent in first position.

In yet another of its aspects, the present invention provides a process for producing a stent comprising a proximal end and a distal end in communication with one another, a tubular wall disposed between the proximal end and the distal end, the tubular wall having a longitudinal axis and a porous surface defined by a plurality of interconnecting struts, a series of the struts connected to one another at an interconnection point, the struts being reversibly hingable at the interconnection point between a first, unrestrained, contracted position and a second position, expanded position, the process comprising the steps of:

(i) selectively removing portions of a solid tubular wall having a diameter substantially the same as that of the stent in the second position to produce a multiple-stent tube defined by multiple sections of the porous surface connected to one another by a series of radially disposed connecting members;

(ii) radially compressing the multiple-stent tube such that the multiple sections have a diameter substantially the same as that of the stent in the first position; and (iii) removing the connecting members between the multiple sections to produce the stent in the first position.

Thus, the present inventor has developed a novel stent which is fundamentally different from stents produced heretofore. The present stent is expandable from a first, contracted position to a second, expanded position without the stent undergoing significant plastic deformation throughout its structure. Further, in the first, contracted position the present stent, unlike the stent of Lau described above, has no mechanical forces stored therein. Accordingly, a distinct advantage of the present stent over the stent of Lau is that, in the contracted state, the present stent does not have to be mechanically restrained—i.e., in the present stent may be consider to be mechanically unrestrained in the contracted state. A preferred feature of the present stent is that, in the contracted state, it generally assumes the structure of a tubular wall having a substantially circular cross-section. A further preferred feature of the present stent is that it has substantially the same cross-sectional shape in the first, contracted (i.e, unexpanded) state and the second, expanded shape. When compared to the stent of Lau and Fishcell, this feature of the present stent is advantageous since it facilitates even expansion of the stent during deployment.

In the present stent, a series of the struts defining the porous surface of the stent are connected at an intersection point. This intersection point actually functions as a hinge about which the stent may be transformed from the contracted state to the expanded state or vice versa. For, example, when the stent is transformed from the contracted state to the expanded state, this generally occurs by a widening of the angle between adjacent struts at the intersection point instead of plastic deformation of the entire network of struts. Specifically, the intersection point (only) undergoes a minor plastic bending during hinging of the stent between the contracted and expanded states. However, since plastic deformation of the entire network of the struts is avoided in the present stent, the occurrence of microcracks on and/or uneven thinning of the stent surface is significantly reduced or eliminated.

Another advantage accruing from a preferred embodiment of the present stent is that, since the stent expands by hinging open of the struts at the intersection point, the change in the longitudinal dimension of the stent during expansion is substantially negligible. This advantage of the present stent is facilitated by a preferred feature of providing a compression means in one or more of the longitudinally disposed struts. If present stent, the specific shape of the compression means disposed in the longitudinal strut is not particularly restricted provided that it serves to minimize or inhibit lengthening of the stent when it is transformed from the unexpanded state to the expanded state, or vice versa. Preferably, the compression means comprises at least one lateral section disposed in the longitudinal strut, more preferably at least a first lateral section and a second lateral section disposed in the longitudinal strut. By "lateral section" is meant a section of the longitudinal strut which is bowed in or out of (i.e., radially from) the strut. The apex of the lateral section may be pointed, rounded or substantially flat. When the compression means comprises a first lateral section and a second lateral section, the two sections may be symmetric or asymmetric (in the case of asymmetric this includes two sections of the same shape but different size and two sections of different and size). Further, when the compression means comprises a first lateral section and a section lateral section, the sections may be bowed in the same or opposite direction.

A particularly preferred embodiment of the compression means comprises a sinusoidal or S-shaped section (an example of such a section is illustrated herein and discussed below).

As will be described in more detail hereinbelow, the present process essentially comprises starting with a tubular wall having a porous surface defined by a plurality of interconnecting struts and thereafter hinging or compressing the tubular wall, in essence, to produce the stent in an unrestrained, contracted state. An advantage of this approach is that the desired porous surface after deployment of the stent is conferred to the tubular wall during production of the stent. A further advantage of this approach is that the present stent may be hinged between the first, contracted (i.e., unexpanded) position and the second, expanding position without the need to produce an intermediate position. Specifically, unlike the approach in Fischell of having distinct unfolded pre-deployment (i.e., post-production/no balloon), folded pre-deployment (i.e., on balloon) and post-deployment forms of the stent, as will be developed below, the present approach is initially to produce the stent in the desired final form (i.e., the second, expanded position) and thereafter radially compress the stent to a predeployment form (i.e., the first, contracted position). The advantage of the present approach is that expansion of the stent to the second, expanded position is greatly facilitated.

Thus, some of the advantages accruing from the present stent may be summarized as follows:

(i) the stent is produced initially in the desired configuration, then radially compressed (or otherwise folded) to a contracted position and finally returned to the original desired configuration via expansion by a balloon or other mechanical means thereby simplifying production and use;

(ii) in the deployed stent, the structure of the stent has not undergone any plastic deformation which obviates or mitigates the occurrence of micro-cracks and/or thinning; and (iii) since the structure of the present stent does not undergo plastic deformation, the occurrence of recoil in the deployed stent is obviated or mitigated (this is a major advantage of the present stent).

As will be apparent below, there are also many processing advantages which accrue from the present process. These include: (i) elimination of conventional remelt removal steps, and (ii) more efficient electropolishing and radio-opaque marker (e.g. gold) deposition steps, when these steps are used in conjunction with the present process.

BRIEF DESCRIPTION OF THE DRAWINGS

Embodiments of the present invention will be described with reference to the accompanying drawings wherein like numerals designate like parts and in which.

BEST MODE FOR CARRYING OUT THE INVENTION

The specific design of the porous surface is not particularly restricted. Preferably, in the expanded state, at least two of the struts meet at the intersection point to define an acute angle. As will be developed hereinbelow, as the stent is radially compressed from the expanded state to the contracted state, this acute angle becomes further reduced.

In the context of the present stent, various repeating patterns in the porous surface of the tubular wall are particularly advantageous. Generally, the preferred repeating pattern is a polygon having a pair of side walls substantially parallel to the longitudinal axis of the stent passageway in question, a first concave-shaped wall and a second convex-shaped wall connecting the side walls. Various preferred repeating patterns which are useful in the context of the present stent are disclosed in the following copending patent applications:

Canadian patent application number 2,134,997 (filed Nov. 3, 1994);

Canadian patent application number 2,171,047 (filed Mar. 5, 1996);

Canadian patent application number 2,175,722 (filed May 3, 1996);

Canadian patent application number 2,185,740 (filed Sep. 17, 1996);

International patent application PCT/CA97/00151 (filed Mar. 5, 1997); and

International patent application PCT/CA97/00152 (filed Mar. 5, 1997);

the contents of each of which are hereby incorporated by reference.

The present stent may be constructed from any suitable starting material. Preferably, the starting material is a thin tube of a metal or alloy. In one preferred embodiment, the starting material may be one which is plastically deformable—non-limiting examples of such a material include stainless steel, titanium, tantalum and the like. In another preferred embodiment, the starting material may be one which expands via temperature-dependent memory (i.e., a material which will expand upon reaching a certain temperature)—non-limiting examples of such a material include nitinol and the like. In this embodiment, the use of such a temperature-dependent memory is greatly facilitated when compared to the prior art use of these materials. The prior art approach when using such materials has been to produce the stent in the unexpanded state and thereafter condition the stent to have a specific transition temperature by the successive steps of: (i) chilling, (ii) expanding, and (iii) heat annealing the structure, until the expanded state has been reached. Such conditioning subjects the structure to significant stretching (again this gives rise to the likelihood of the occurrence of thinning and micro-crack formation in the stent structure). In contrast, in the present invention, there is no requirement to condition the material in such an extreme manner. Rather, the stent is produced in the expanded state, heat annealed in this state, chilled and radially compressed (as will be described below) to a contracted stated, all without subjecting the structure to expansion and stretching. In some cases, it may be desirable to restrain the stent in the contracted state.

The stent of the present invention may further comprise a coating material thereon. The coating material may be disposed continuously or discontinuously on the surface of the stent. Further, the coating may be disposed on the interior and/or the exterior surface(s) of the stent. The coating material may be one or more of a biologically inert material (e.g. to reduce the thrombogenicity of the stent), a medicinal composition which leaches into the wall of the body passageway after implantation (e.g. to provide anticoagulant action, to deliver a pharmaceutical to the body passageway and the like) and the like.

The stent is preferably provided with a biocompatible coating, in order to minimize adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in published International patent applications WO-A-93/16479 and WO-A-93/15775. Polymers described in those specifications are hemo-compatible as well as generally biocompatible and, in addition, are lubricious. When a biocompatible coating is used, It is important to ensure that the surfaces of the stent are completely coated in order to minimize unfavourable interactions, for instance with blood, which might lead to thrombosis.

This good coating can be achieved by suitable selection of coating conditions, such as coating solution viscosity, coating technique and/or solvent removal step. The coating, if present, can be applied to the stent in the expanded or contracted state. Preferably, the stent is applied to the coating in the contracted state.

Figure 1:
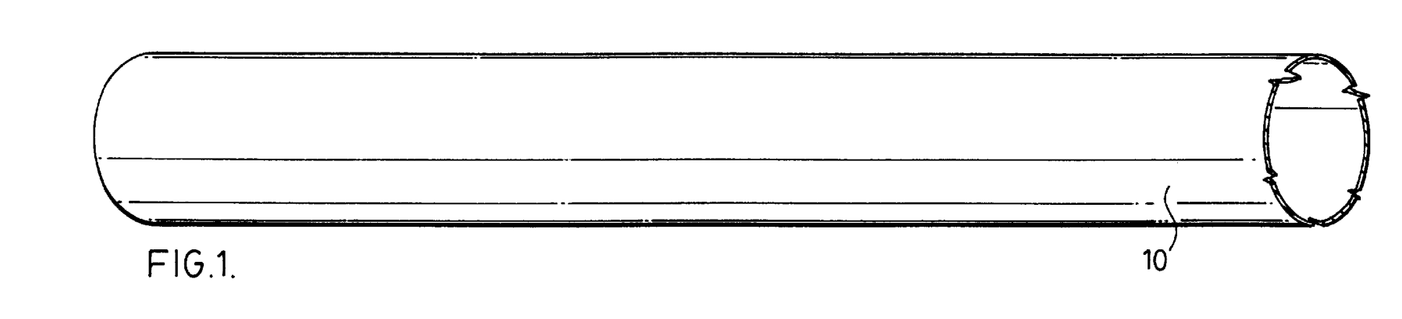
FIG. 1 illustrates a perspective view of a solid tubular wall useful in a preferred initial step in the present process.

With reference to FIG. 1, there is illustrated a side elevation of a solid tube 10 of a starting material for the present process. The nature of solid tube 10 is not particularly restricted and includes all materials conventionally used to produce stents. In one preferred embodiment, solid tube 10 is constructed of a plastically deformable material. As discussed above, a non-limiting example of such a material is stainless steel. In another preferred embodiment, solid tube 10 is constructed of a material which will expand when a certain temperature is reached. In this embodiment, the material may be a metal alloy (e.g. nitinol) capable of self-expansion at a temperature of at least about 30° C., preferably in the range of from about 30° to about 40° C. Preferably, solid tube 10 has a thickness in the range of from about 0.003 to about 0.015 inches.

Solid tube 10 is then subjected to processing which results in removal of a portion thereof to define a porous surface. While the precise nature of this processing is not particularly restricted, it is preferred that the processing by effected on a computer programmable, laser cutting system.

Figure 2:
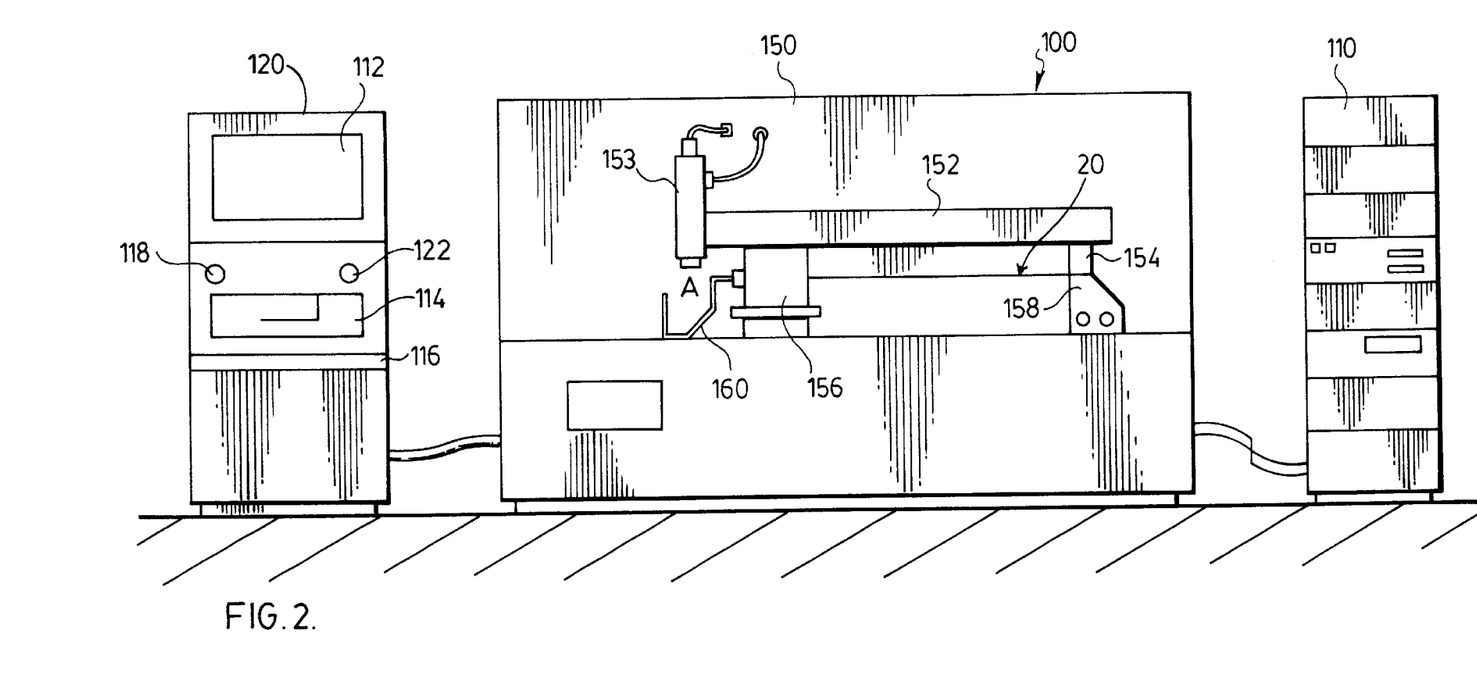
FIG. 2 illustrates a schematic of a programmable, computer controlled laser cutting system useful in a preferred step of the present process.

With reference to FIG. 2, there is illustrated, as an example, a schematic for a suitable such laser cutting system 100. System 100 comprises a power supply 110, a computer console 120 and a work station 150. Power supply 110 is conventional. Computer console 120 is also conventional and comprises a monitor 112, a computer 114, a keyboard, 116, a system start switch 118 and system stop switch 120. Work station 150 comprises a laser 152 mounted on a pair of supports 154,156. Laser 152 comprises a laser emission head 153. Support 154 is in turn supported on a support 158. The combination of supports 154,158 is adapted to have an opening therebetween for receiving a tubular material. The combination of supports 154,158 may be adapted to be moveable toward support 156 thereby supporting the tubular material as it is fed under head 153. Alternatively, supports 154,158 may be fixed within work station 150 and a supplementary, moveable support (not shown) may be provided for supporting the tubular material as it is fed under head 153. Support 156 is adapted to receive and translate a tubular starting material therethrough in the general direction of head 153. A basin 160 is disposed below head 153. A suitable such system is known in the art as the LPLS-100 Series Stent Cutting Machine.

In the context of the present process, system 100 may be operated in the following manner. Solid tube 10 is placed in work station 150 by guiding an end thereof into support 156 and supporting the opposite end thereof between supports 154,158. Solid tube 10 is then fed through support 156 to a region A wherein a laser beam is emitted from head 153 and serves to cut solid tube 10 to produce a porous surface thereof having a preselected design.

Figure 3:
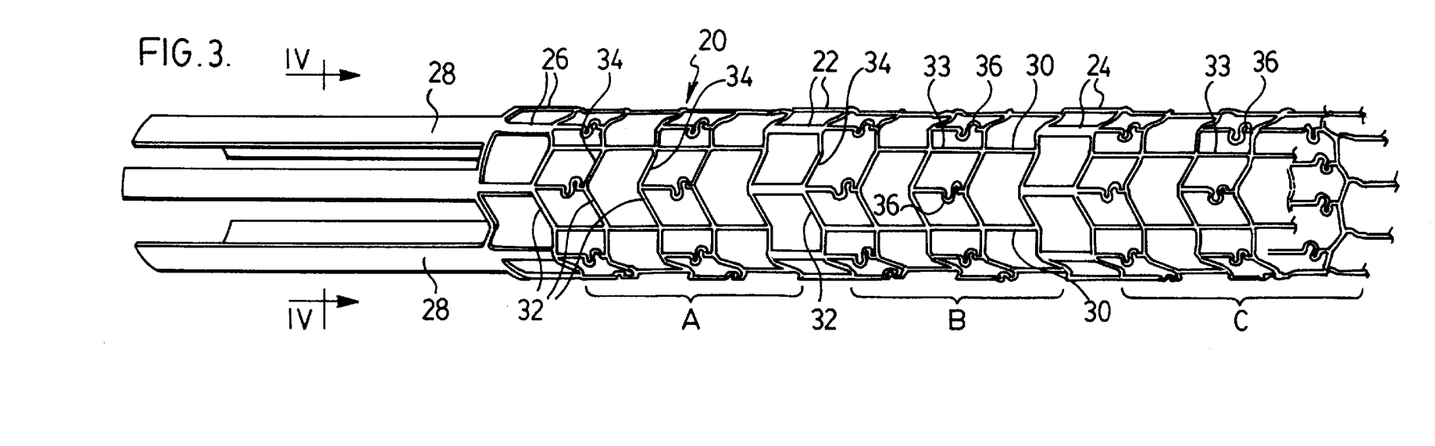
FIG. 3 illustrates a perspective view of the tubular wall in FIG. 1 after selective removal of portions thereof.
Figure 4:
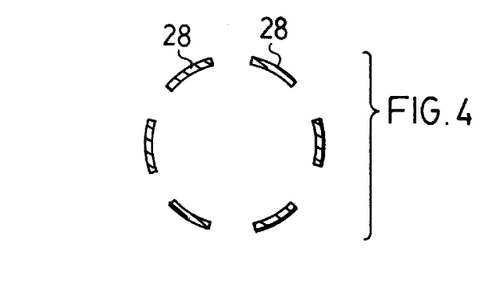
FIG. 4 illustrates a section along line IV—IV in FIG. 3.

A preferred product of laser cutting system 100 is illustrated in FIG. 3 as a multiple stent tube 20—this can be made of a plastically deformable material such as stainless steel or a temperature-dependent memory material such as nitinol. In the illustrated embodiment, multiple stent tube 20 comprises three distinct stent sections A,B,C. Multiple stent tube 20 may comprise many more stent sections (not shown) and, in practice, may be up to 1 metre or more in length. It will be appreciated by those of skill in the art that, for illustrative purposes, the porous surface of each stent section A,B,C is somewhat abbreviated (i.e., number rings of polygons). Stent section A is connected to stent section B by a plurality of connecting tabs 22. Similarly, stent section B is connected to stent section C by a plurality of connecting tabs 24. At one end of multiple stent tube 20 is a plurality of generally elongate pull tabs 28. Stent section A is connected to pull tabs 28 by a plurality of connecting tabs 26. As illustrated, each ring of connecting tabs 22,24,26 and the ring of pull tabs 28 are in spaced relationship to one another.

As illustrated in FIG. 3, each of stent sections A,B,C comprises a tubular wall having a porous surface. The porous surface is made up of a plurality of longitudinal struts 30, first radial struts 32 and second radial struts 34. Some of longitudinal struts 30 comprise a compressible portion 36. Longitudinal connecting members 33 are disposed between adjacent compressible portions 36. As will be appreciated by those of skill in the art, and having regard to the disclosure hereinbelow, the curvature of compressible portion 36 in FIG. 3 has been exaggerated for illustrative purposes only.

Figure 5:
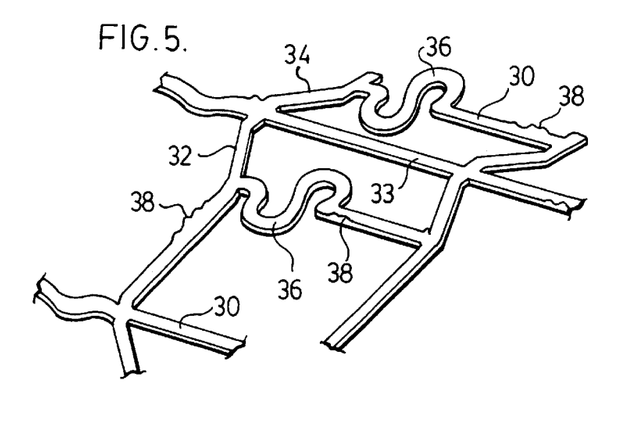
FIGS. 5 and 6 illustrate explode views of a portion of the tubular wall illustrated in FIG. 3.
Figure 6:
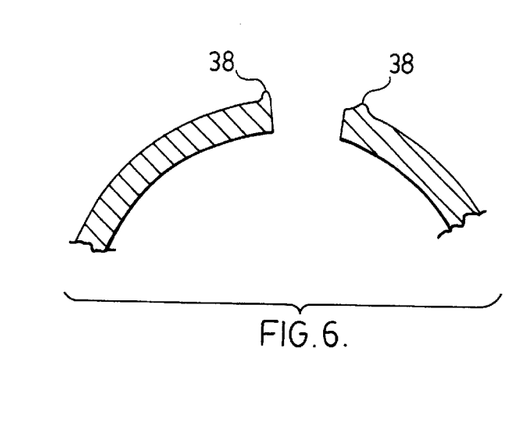

With reference to FIGS. 5 and 6, there are illustrated exploded portions of multiple stent tube 20. As illustrated, multiple stent tube 20, as it emanates from laser cutting system 100, comprises a number of remelt portions 38. The formation of such remelt portions is a conventional byproduct of precision laser cutting techniques. Normally, such remelt portions may be removed by labour-intensive techniques such as buffing, polishing or chemical post-processing. As will be developed below, an advantage accruing from the present process is that such labour-intensive polishing techniques may be obviated by the present process.

Figure 7:
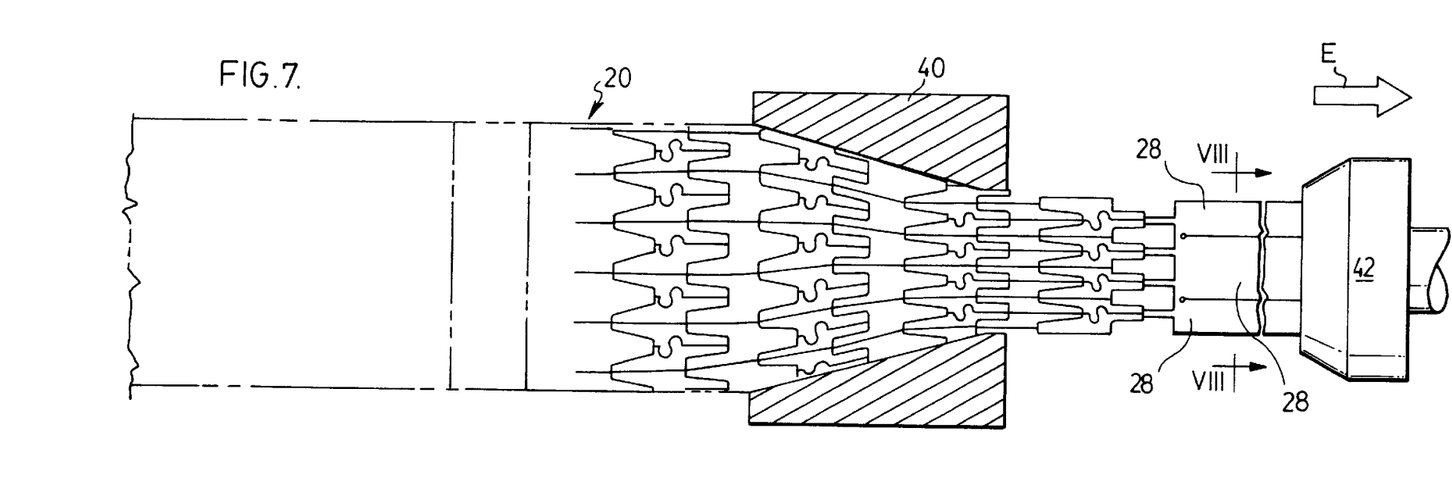
FIG. 7 illustrates a side elevation of a preferred step of the present process.

With reference to FIG. 7, the leading edges of pull tabs 28 of multiple stent tube 20 are fed to a sink die 40 having a tapered cross-section. Pull tabs 28 are clamped into a hydraulic puller 42 by any suitable means (not shown). Hydraulic puller 42 is then actuated in the direction of arrow E thereby effectively pulling multiple stent tube 20 through sink die 40. In FIG. 7, for clarity, connecting tabs 22,24,26 have been omitted. If multiple stent tube 20 is constructed of a material which expands via temperature-dependent memory, it is desirable to chill sink die 40 and/or spray liquid nitrogen over multiple stent tube 20 to facilitate radial compression thereof. Further, it may be desirable to place a sheath (not shown) around each of stent sections A,B,C as they emanate from sink die 40.

As will be appreciated by those of skill in the art, the inlet of sink die 40 has a diameter equivalent to the outer diameter of the stent in a deployed state whereas the outlet of sink die 40 has a diameter equivalent to the desired diameter of the stent in an unexpanded state. As will further be appreciated by those of skill in the art, connecting tabs 22,24,26 and pull tabs 28 are of a width such that, during pulling of multiple stent tube 20 through sink die 40, they are generally unaffected. Rather, pulling of multiple stent tube 20 through sink die 40 confers various forces, discussed in more detail hereinbelow, on stent sections A,B,C. An advantage accruing from passing multiple stent tube 20 through sink die 40 is that remelt portions 38 existing on the former will be significantly or completely removed by friction. This minimizes or avoids the need to utilize a separate labour-intensive polishing and buffing techniques to remove remelt portions 38.

With further reference to FIG. 7, those of skill in the art will also appreciate that at least a portion of each interconnected pair of first radial strut 32 and second radial strut 34 form an acute angle (i.e., the angle between interconnected first radial strut 32 and second radial strut 34 is less than about 90°) opening away from sink die 40. It is believed that the present process will also be useful in the case where interconnected pairs of first radial strut 32 and second radial strut 34 form an obtuse angle (i.e., the angle between interconnected first radial strut 32 and second radial strut 34 is greater than about 90° but less than 180°).

Figure 8:
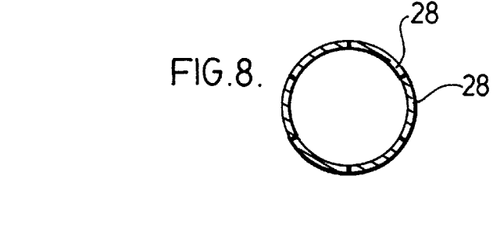
FIG. 8 illustrates a section along line VIII—VIII in FIG. 7.

With reference to FIG. 8, it will be apparent to those of skill in the art that the arc length of each pull tab 28 is selected such that the aggregate thereof for all of pull tabs 28 is equivalent to the circumference of the stent in the unexpanded state.

Figure 9:
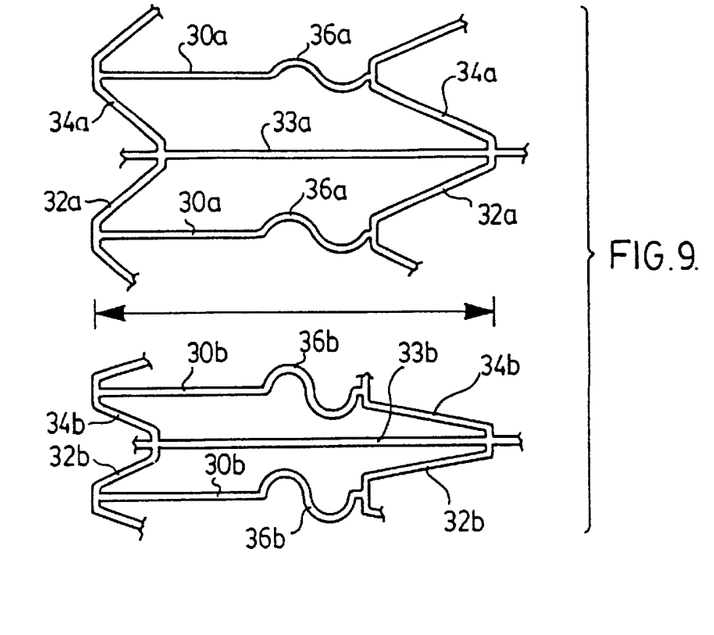
FIGS. 9 and 10 illustrate exploded views of a portion of the tubular wall before and after processing as illustrated in FIG. 7.
Figure 10:
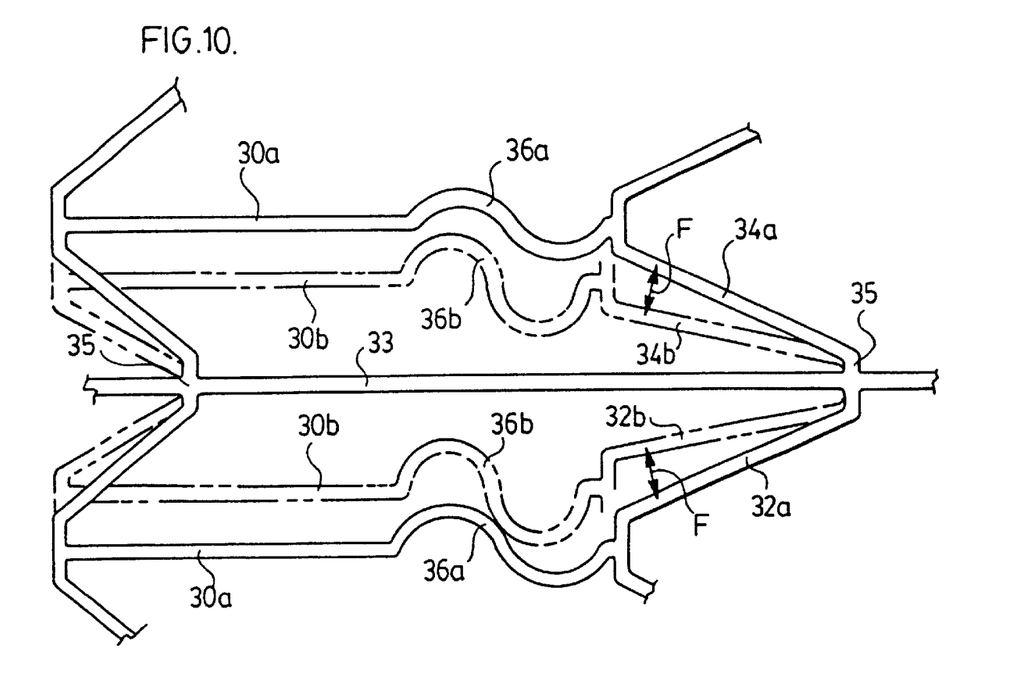

With reference to FIGS. 9 and 10, the action of pulling multiple stent tube 20 in the direction of arrow E on stent sections A,B,C will be described in more detail. To facilitate this discussion, the suffix "a" will be used to denote common elements of stent sections A,B,C prior to sink die 40 (FIG. 7) and the suffix "b" will be used to denote common elements of stent sections A,B,C after sink die 40 (FIG. 7). Thus, upon the pulling of multiple stent tube 20 through sink die 40 in the direction of arrow E (FIG. 7), sink die 40 confers onto stent section A,B,C radial forces in the direction of arrows F (FIG. 10). This results in plastic bending at an intersection point 35 of first radial strut 32 and second radial strut 34. As illustrated, no plastic deformation of the stent section occurs. Further, the overall length of the stent section is unchanged by virtue of the combination of: (i) compression of compressible portion 36 disposed in longitudinal strut 30, and (ii) the presence of longitudinal connecting member 33 disposed between adjacent compressible portions 36. Ideally, compressible portion 36 and longitudinal connecting member 33 are designed so that less force is required to compress portion 36 than is required to stretch longitudinal connecting member 33 (i.e., the ratio of the force required to stretch longitudinal connecting member 33 to the force required to compress portion 36 is greater than 1). This design preference is more prevalent in the contracted (i.e., unexpanded) state of the stent leading to improved flexibility and less prevalent in the expanded state of the stent leading to improved radial rigidity. The ability to maintain the length of stent section substantially constant is a key advantage of the present process and the resulting stent. Thus, connection point 35 is functioning as a solid state hinge which allows for radial compression of multiple stent tube 20 without lengthening thereof while avoiding any appreciable plastic deformation of struts 30,32,33,34.

Figure 11:
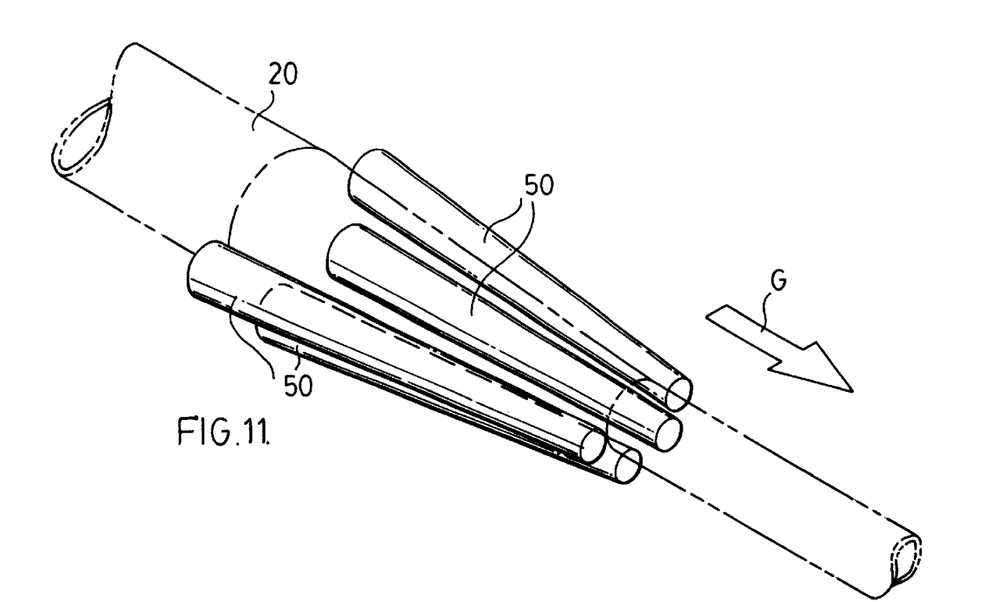
FIGS. 11–13 illustrate a first alternative to the step of the present process illustrated in FIG. 7.
Figure 12:
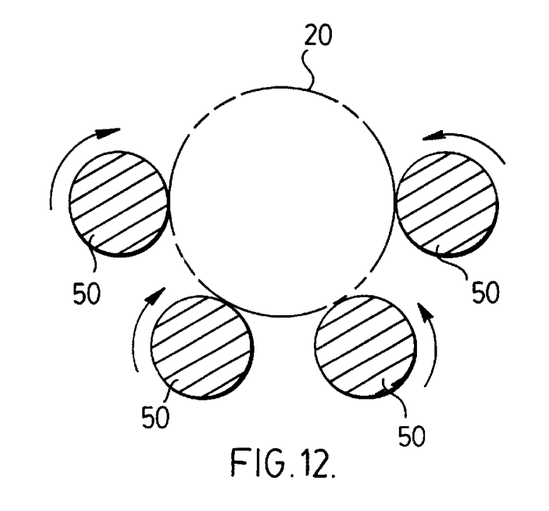
Figure 13:
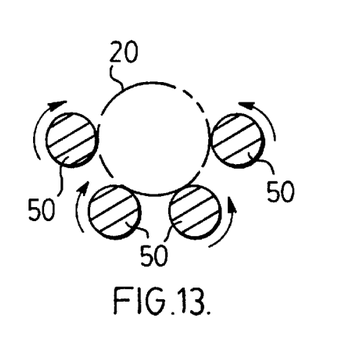

With reference to FIGS. 11–13, there is illustrated an alternate embodiment to the sink die/hydraulic puller embodiment illustrated in FIG. 7 hereinabove. In this embodiment, a plurality of longitudinal rollers 50 is arranged to provide a generally U-shaped trough having a tapered cross-section. Further, each longitudinal roller 50 itself has a tapered cross-section. In use, multiple stent tube 20 (in this embodiment, the creation of pull tabs 28 would not be required) is fed to the plurality of longitudinal rollers 50 in the direction of arrow G. Longitudinal rollers 50 are rotated in the directions illustrated in FIGS. 12 and 13 by any suitable means (not shown). This results in radial compression of multiple stent tube 20 as discussed hereinabove with reference to FIGS. 9 and 10. Of course, while four longitudinal rollers 50 have been illustrated, those of skill in the art will readily appreciate that the specific number of rollers used in this embodiment is not particularly restricted.

Figure 14:
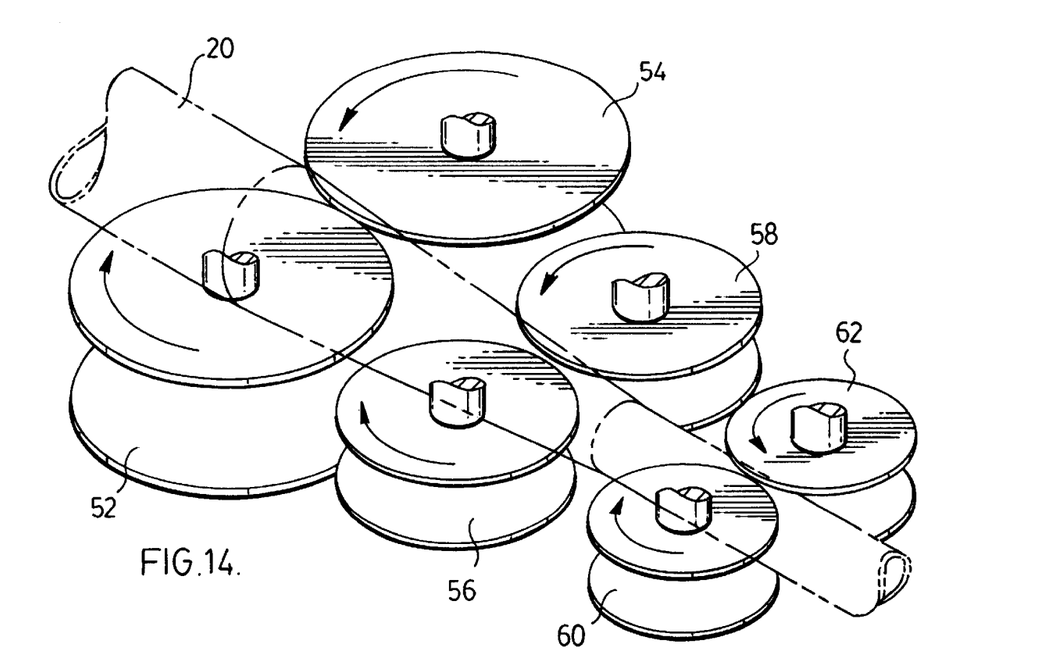
FIGS. 14 and 15 illustrate a second alternative to the step of the present process illustrated in FIG. 7.
Figure 15:
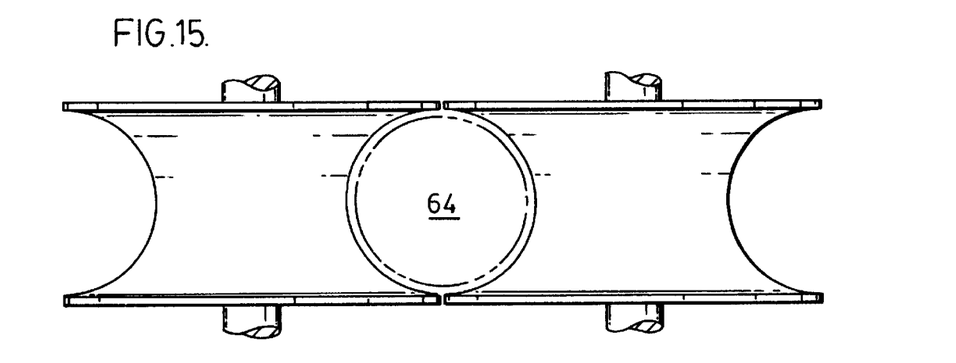

With reference to FIGS. 14 and 15, there is illustrated yet a further alternative to the sink die/hydraulic puller illustrated in FIG. 7. In this embodiment, a series of paired rollers defining an opening of decreasing diameter is used to radially compress multiple stent tube 20 in the manner described hereinabove with reference to FIGS. 9 and 10. As illustrated, an initial pair of rollers 52,54 is provided for receiving multiple stent tube 20. This is followed by an intermediate pair of rollers 56,58 which, in turn, are followed by a final pair of rollers 60,62. With reference to FIG. 15, the cross-section of the pairs of rollers presented to multiple stent tube 20 is illustrated. As illustrated, each pair of rollers combines to define an opening 64 through which multiple stent tube 20 passes. Thus, the size of opening 64 defined by rollers 52,54 approximate the diameter of multiple stent tube 20. Successive pairs of rollers 56,58 and 60,62 are adapted such that opening 64 is progressively decreased. In this embodiment, the formation of pull tabs 28 as illustrated in FIG. 7 is not required. Of course, while three pairs of rollers have been illustrated, those of skill in the art will readily appreciate that the specific number of rollers used in this embodiment is not particularly restricted.

Figure 16:
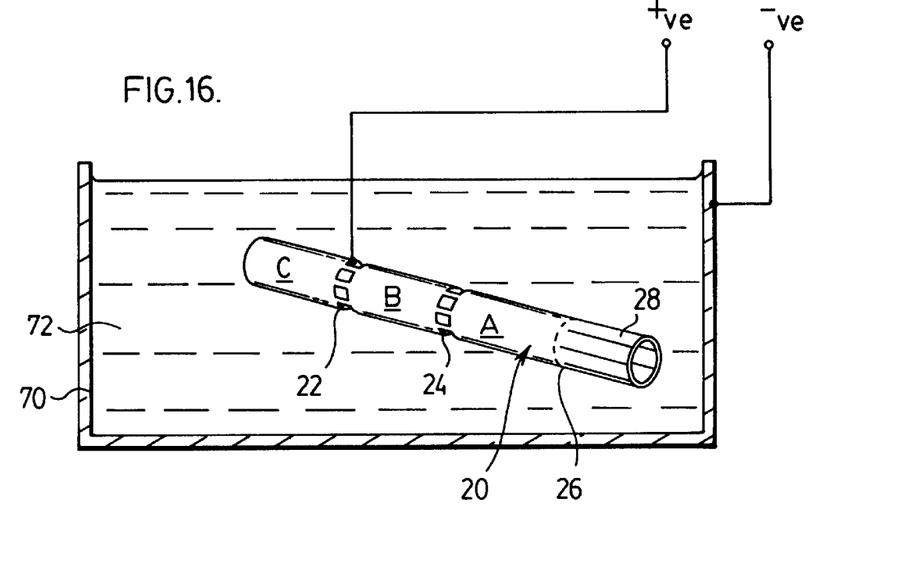
FIG. 16 illustrates a schematic of a electropolishing step preferably used in the present process.

With reference to FIG. 16, a preferred step in the present process is illustrated. Here, multiple stent tube 20 is subjected to an electropolishing step. Generally, electropolishing is done in a container 70 having dispensed therein a liquid 72 which functions both as an electrolyte and a chemical etchant for removal of a thin layer of material from multiple stent tube 20. Conventionally, individual stents are placed in container 70 for treatment in this fashion. Typically, container 70 functions as one electrode and the stent is directly connected to the other electrode. Electrolysis is then conducted facilitating chemical etching resulting in electropolishing of the stent. A distinct disadvantage in the prior art approach is the requirement that a portion of the stent be directly connected to one electrode since the result of this is that electropolishing will not take place at the connection point. A distinct advantage of the present process is that multiple stent tube 20 can be directly connected to one of the electrodes via one or more of the connection tabs (i.e., one or more of connecting tabs 22,24,26) or pull tabs (if present, i.e., pull tabs 28) of multiple stent tube 20. Since these connecting tabs/pull tabs (if present) do not form part of the finished stent (discussed hereinbelow), it is of no consequence that electropolishing does not take place on the portion of multiple stent tube 20 which is directly connected to the electrode. The precise details of the selection and operation of equipment and materials (i.e., electrodes, electrolyte, etchant, voltage, current and the like) need to achieve electropolishing are within the preview of a person skilled in the art and will not be discussed in further detail herein.

Figure 17:
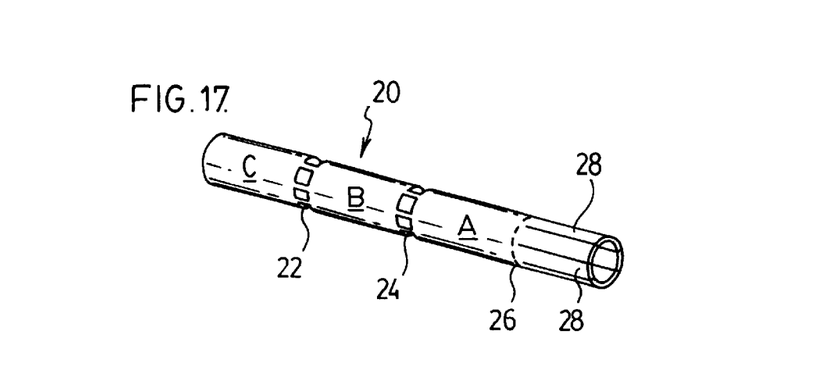
FIG. 17 illustrates a schematic of a gold deposition step preferably used in the present process.

Electropolished multiple stent tube 20, now illustrated in FIG. 17, may then be passed to a radio-opaque marker application station (not shown). Typically, for stainless steel stents, it is conventional to apply a gold marker to the surface thereof to facilitate positioning of the stent by the physician. This is required because stainless steel is transparent to the radiography techniques normally used to position the stent. Conventionally, the marker is disposed on each individual stent as one of the last steps in the manufacturing process. This renders marker application as the majority of expense in the overall manufacture of stainless steel stents. As described hereinabove, multiple stent tube 20 contains a number of stents and can be of a length up to 1 metre or more. This renders multiple stent tube 20 much easier to handle than individual stents and significantly reduces the costs of applying a radio-opaque marker—this is a significant advantage of the present process.

Figure 18:
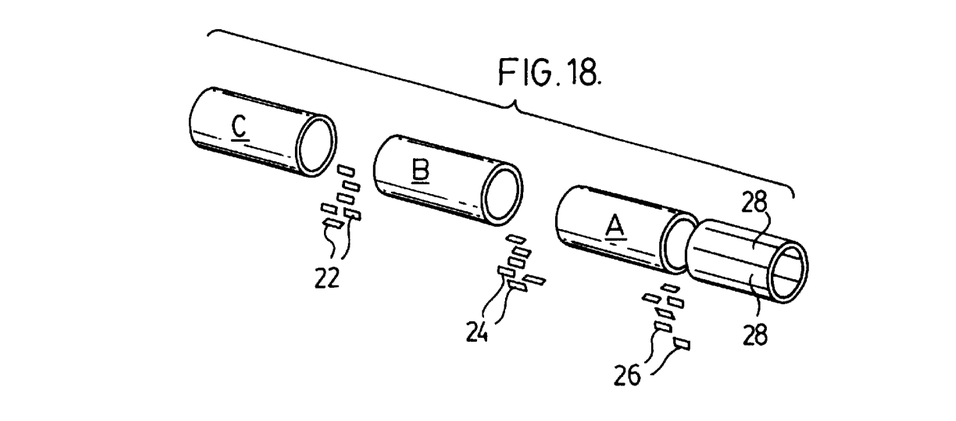
FIG. 18 illustrates a preferred, final step in the present process.

A final preferred step in the present process is illustrated schematically in FIG. 18. As illustrated, multiple stent 20 is subjected to a laser (or other) cutting technique effectively to remove connecting tabs 22,24,26 and pull tabs 28. The precise nature by which this is achieved is not particularly restricted and is within the preview of a person of ordinary skill in the art.

Thus, the product of the final step illustrated in FIG. 18 is a plurality of stent sections A,B,C, together with scrap by products comprising connecting tabs 22,24,26 and pull tabs 28. Thus, the illustrated embodiment of the present process may be regarded as a batch process, wherein a batch of stents is made from a single length of tubular starting material. The length of the tube is not particularly restricted in the context of the invention and is more dependent on the practical size of equipment used to treat the tubular starting material (e.g. the laser cutting system).

The stent produced according to the present process may be used in a conventional manner. The significant advantage of the present stent is that it may be expanded by unhinging of first radial struts 32 and the second radial struts 34 about connection point 35. This is effected by a plastic bending at connection point 35. Thus, the important advantages of the present stent are: (i) it may be produced such that it does not need to be restrained in the unexpanded state; (ii) expansion of the stent in a lumen may be effected without the occurrence of plastic deformation of struts 32,34,36; and (iii) expansion of the stent in a lumen may be effected without any appreciable change in the length of the stent—to the knowledge of the Applicant, a stent having this combination of features heretofore has been unknown. A stent having these advantages mitigates or obviates the occurrence of thinning and/or micro-cracks in the expanded stent to which prior stents have been susceptible.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments.

What is claimed is:

1. A process for producing a stent comprising a proximal end and a distal end in communication with one another, a tubular wall disposed between the proximal end and the distal end, the tubular wall having a longitudinal axis and a porous surface defined by a plurality of interconnecting struts, a series of the struts connected to one another at an interconnection point, the struts being reversibly hingable and plastically bendable at the interconnection point between a first, unrestrained contracted position and a second, expanded position, the process comprising the steps of:
   (i) selectively removing portions of a solid tubular wall having a diameter substantially the same as that of the stent in the second position to define multiple sections of the porous surface connected to one another by a series of axially disposed connecting members;
   (ii) radially compressing the stent in the second position to plastically bend the struts at the interconnection point thereby producing the stent in the first position, said radially compressing step comprising the step of applying a radially inward force on the multiple sections and the connecting members such that the multiple sections have a diameter substantially the same as that of the stent in the first position; and
   (iii) removing the connecting members between the multiple sections to produce the stent in the first position.

2. The process defined in claim 1, wherein the stent is passed though a radially tapered die.

3. The process defined in claims 1, wherein the porous surface is produced by selectively removing portions of a solid tubular wall having a diameter substantially the same as that of the stent in the second position.

4. The process defined in claim 1, wherein the porous surface is produced by laser cutting portions of the solid tubular wall.

5. The process defined in claim 1, wherein prior to Step (iii), the tubular wall is subjected to an electro-polishing step.

6. The process defined in claim 1, wherein prior to Step (iii), the tubular wall is subjected to a metal deposition step.

7. The process defined in claim 6, wherein the metal deposition step comprises depositing gold on to selected portions of the tubular wall.

8. The process defined in claim 1, wherein Step (i) comprises laser cutting sections of the solid tubular wall.

9. The process defined in claim 1, wherein Step (ii) comprises passing the tubular wall through a radially tapered die.

10. The process defined in claim 1, wherein Step (i) further comprises defining tabs at one end of the tubular wall.

11. The process defined in claim 10, wherein the tubular wall is pulled by the tabs through a radially tapered die.

12. The process defined in claim 1, wherein prior to Step (iii), the tubular wall is subjected to an electro-polishing step.

13. The process defined in claim 1, wherein prior to Step (iii), the tubular wall is subjected to a metal deposition step.

14. The process defined in claim 13, wherein the metal deposition step comprises depositing gold on to selected portions of the tubular wall.

* * * * *